(12) United States Patent
Hodoshima et al.

(10) Patent No.: US 10,556,229 B2
(45) Date of Patent: Feb. 11, 2020

(54) COMPOSITE CATALYST, METHOD FOR PRODUCING COMPOSITE CATALYST, METHOD FOR PRODUCING LOWER OLEFIN AND METHOD FOR REGENERATING COMPOSITE CATALYST

(71) Applicant: CHIYODA CORPORATION, Yokohama-shi, Kanagawa (JP)

(72) Inventors: Shinya Hodoshima, Yokohama (JP); Fuyuki Yagi, Yokohama (JP); Azusa Motomiya, Yokohama (JP); Shuhei Wakamatsu, Yokohama (JP)

(73) Assignee: CHIYODA CORPORATION, Yokohama (JP)

( * ) Notice: Subject to any disclaimer, the term of this patent is extended or adjusted under 35 U.S.C. 154(b) by 0 days.

(21) Appl. No.: 15/501,088

(22) PCT Filed: Jul. 31, 2015

(86) PCT No.: PCT/JP2015/071761
§ 371 (c)(1),
(2) Date: Feb. 1, 2017

(87) PCT Pub. No.: WO2016/017794
PCT Pub. Date: Feb. 4, 2016

(65) Prior Publication Data
US 2017/0252731 A1  Sep. 7, 2017

(30) Foreign Application Priority Data
Aug. 1, 2014 (JP) .................. 2014-157518

(51) Int. Cl.
| | |
|---|---|
| *B01J 29/06* | (2006.01) |
| *B01J 29/76* | (2006.01) |
| *B01J 29/90* | (2006.01) |
| *C07C 4/06* | (2006.01) |
| *B01J 29/88* | (2006.01) |
| *B01J 29/87* | (2006.01) |
| *B01J 29/072* | (2006.01) |
| *B01J 29/46* | (2006.01) |
| *B01J 37/00* | (2006.01) |
| *B01J 21/08* | (2006.01) |
| *B01J 37/04* | (2006.01) |
| *B01J 37/06* | (2006.01) |
| *B01J 37/10* | (2006.01) |
| *B01J 37/30* | (2006.01) |
| *B01J 38/12* | (2006.01) |

(52) U.S. Cl.
CPC ............ *B01J 29/76* (2013.01); *B01J 21/08* (2013.01); *B01J 29/061* (2013.01); *B01J 29/072* (2013.01); *B01J 29/46* (2013.01); *B01J 29/87* (2013.01); *B01J 29/88* (2013.01); *B01J 29/90* (2013.01); *B01J 37/0009* (2013.01); *B01J 37/0018* (2013.01); *B01J 37/04* (2013.01); *B01J 37/06* (2013.01); *B01J 37/10* (2013.01); *B01J 37/30* (2013.01); *C07C 4/06* (2013.01); *B01J 38/12* (2013.01); *B01J 2229/183* (2013.01); *B01J 2229/30* (2013.01); *B01J 2229/42* (2013.01); *C07C 2521/08* (2013.01); *C07C 2529/46* (2013.01); *C07C 2529/76* (2013.01); *C07C 2529/87* (2013.01)

(58) Field of Classification Search
CPC ........ B01J 29/072; B01J 29/061; B01J 29/46; B01J 29/76; B01J 29/87; B01J 29/88; B01J 2229/30; B01J 2229/183; B01J 2229/42; B01J 37/10; B01J 37/0009; B01J 38/12; B01J 37/04; B01J 37/06; B01J 3737/30; B01J 37/0018; C07C 2529/76; C07C 2529/46; C07C 2529/88; C07C 2529/87; C07C 2521/08; C07C 4/06
USPC ........ 502/60, 61, 63, 64, 66, 69, 71, 74, 77, 502/34, 38; 585/648, 653
See application file for complete search history.

(56) References Cited

U.S. PATENT DOCUMENTS

2015/0174565 A1* 6/2015 Hodoshima .............. B01J 29/87
585/653

FOREIGN PATENT DOCUMENTS

| | | |
|---|---|---|
| EP | 186395 A2 | 7/1986 |
| EP | 206193 A1 | 12/1986 |
| JP | S61-153143 A | 7/1986 |
| JP | S61-291041 A | 12/1986 |
| JP | H8-217531 A | 8/1996 |
| JP | 2005-520874 A | 7/2005 |
| JP | 2008-222598 A | 9/2008 |
| JP | 2014-24005 A | 2/2014 |
| JP | 2014-24006 A | 2/2014 |
| JP | 2014-24007 A | 2/2014 |
| WO | 2009/018722 A1 | 2/2009 |
| WO | 2010/101121 A1 | 9/2010 |
| WO | 2014-017181 A1 | 1/2014 |

OTHER PUBLICATIONS

Machine translation of JP 06-330055, Nov. 29, 1994.*

(Continued)

*Primary Examiner* — Elizabeth D Wood
(74) *Attorney, Agent, or Firm* — Oliff PLC

(57) ABSTRACT

A lower olefin by using a zeolite catalyst, a composite catalyst capable of further extending the lifetime of catalytic activity, a method for producing the composite catalyst, a method for producing a lower olefin by using the composite catalyst, and a method for regenerating a composite catalyst in the method for producing a lower olefin are provided. The composite catalyst is a catalyst for producing a lower olefin from a hydrocarbon feedstock. This composite catalyst is constituted of a zeolite being a crystalline aluminosilicate containing gallium and iron or iron and further having a framework with 8- to 12-membered ring, and of silicon dioxide. By using the composite catalyst, a lower olefin can be continuously produced over a long period of time.

11 Claims, 6 Drawing Sheets

(56) References Cited

OTHER PUBLICATIONS

Jun. 5, 2018 Office Action issued in Japanese Patent Application No. 2016-538461.
Oct. 6, 2015 Written Opinion issued in International Patent Application No. PCT/JP2015/071761.
Oct. 6, 2015 International Search Report issued in International Patent Application No. PCT/JP2015/071761.
Jan. 9, 2018 Office Action issued in Japanese Patent Application No. 2016-538461.

* cited by examiner

[Fig. 1]

|  | COMPARATIVE EXAMPLE 1 | EXAMPLE 1 | EXAMPLE 2 |
|---|---|---|---|
| ZEOLITE SPECIES | FeGaAl-MFI | FeGaAl-MFI | FeAl-MFI |
| ACID DENSITY(Si/(Fe+Ga+Al))[mol/mol] | 121.3 | 121.3 | 120.3 |
| MOLAR COMPOSITION OF Fe(Fe/(Fe+Ga+Al))[mol/mol] | 0.4 | 0.4 | 0.5 |
| MOLAR COMPOSITION OF Ga(Ga/(Fe+Ga+Al))[mol/mol] | 0.3 | 0.3 | 0.0 |
| MOLAR COMPOSITION OF Al(Al/(Fe+Ga+Al))[mol/mol] | 0.3 | 0.3 | 0.5 |
| BINDER USED FOR MOLDING | ALUMINA | SILICA | SILICA |
| MIXED RATIO OF ZEOLITE/BINDER[wt%/wt%] | 77 / 23 | 74 / 26 | 75 / 25 |

[Fig. 2]

|  | COMPARATIVE EXAMPLE 1 | EXAMPLE 1 | EXAMPLE 2 |
|---|---|---|---|
| COMPOSITE OF ZEOLITE/METAL OXIDE | FeGaAl-MFI / Al$_2$O$_3$ | FeGaAl-MFI / SiO$_2$ | FeAl-MFI / SiO$_2$ |
| ACID DENSITY OF ZEOLITE (Si/(Fe+Ga+Al))[mol/mol] | 121.3 | 121.3 | 120.3 |
| MIXED RATIO OF ZEOLITE/BINDER[wt%/wt%] | 77 / 23 | 74 / 26 | 75 / 25 |
| REACTION TEMPERATURE [°C]/PRESSURE[MPa] | 565 / 0.1 | 565 / 0.1 | 565 / 0.1 |
| AMOUNT OF CHARGED CATALYST[mL] | 2.0 | 2.0 | 2.0 |
| LHSV OF n-HEXANE[h$^{-1}$] | 5.0 | 4.5 | 4.5 |
| INITIAL n-HEXANE CONVERSION[wt%] | 67.3 | 64.2 | 55.2 |
| INITIAL ETHYLENE YIELD[wt%] | 8.2 | 7.4 | 5.8 |
| INITIAL PROPYLENE YIELD[wt%] (PROPYLENE SPACE TIME YIELD[g-C$_3$=/g-zeolite·h]) | 18.1 (1.1) | 15.3 (0.81) | 13.8 (0.73) |
| INITIAL YIELD OF AROMATIC HYDROCARBONS [wt%] | 7.3 | 4.3 | 3.5 |
| CATALYST LIFETIME[h] | 80 | 340 | 330 |
| AMOUNT OF DEPOSITED COKE[wt%] | 24.6 | 4.8 | 4.5 |

[Fig. 3]

| | EXAMPLE 3 | EXAMPLE 1 | EXAMPLE 4 |
|---|---|---|---|
| ZEOLITE SPECIES | FeGaAl-MFI | FeGaAl-MFI | FeGaAl-MFI |
| ACID DENSITY(Si/(Fe+Ga+Al))[mol/mol] | 121.3 | 121.3 | 121.3 |
| MOLAR COMPOSITION OF Fe(Fe/(Fe+Ga+Al))[mol/mol] | 0.4 | 0.4 | 0.4 |
| MOLAR COMPOSITION OF Ga(Ga/(Fe+Ga+Al))[mol/mol] | 0.3 | 0.3 | 0.3 |
| MOLAR COMPOSITION OF Al(Al/(Fe+Ga+Al))[mol/mol] | 0.3 | 0.3 | 0.3 |
| BINDER USED FOR MOLDING | SILICA | SILICA | SILICA |
| MIXED RATIO OF ZEOLITE/BINDER[wt%/wt%] | 68 / 32 | 74 / 26 | 90 / 10 |

[Fig. 4]

| | EXAMPLE 3 | EXAMPLE 1 | EXAMPLE 4 |
|---|---|---|---|
| COMPOSITE OF ZEOLITE/METAL OXIDE | FeGaAl-MFI / $SiO_2$ | FeGaAl-MFI / $SiO_2$ | FeGaAl-MFI / $SiO_2$ |
| ACID DENSITY OF ZEOLITE (Si/(Fe+Ga+Al))[mol/mol] | 121.3 | 121.3 | 121.3 |
| MIXED RATIO OF ZEOLITE/BINDER[wt%/wt%] | 68 / 32 | 74 / 26 | 90 / 10 |
| REACTION TEMPERATURE [°C]/PRESSURE[MPa] | 565 / 0.1 | 565 / 0.1 | 565 / 0.1 |
| AMOUNT OF CHARGED CATALYST (CONTENT OF ZEOLITE) [g] | 1.44 (0.98) | 1.32 (0.98) | 1.09 (0.98) |
| WHSV OF n-HEXANE[$h^{-1}$] | 6.0 | 6.0 | 6.0 |
| INITIAL n-HEXANE CONVERSION[wt%] | 52.8 | 64.2 | 68.7 |
| INITIAL ETHYLENE YIELD[wt%] | 6.0 | 7.4 | 8.0 |
| INITIAL PROPYLENE YIELD[wt%] | 13.6 | 15.3 | 15.6 |
| INITIAL YIELD OF AROMATIC HYDROCARBONS[wt%] | 2.5 | 4.3 | 4.6 |
| CATALYST LIFETIME[h] | 360 | 340 | 480 |
| AMOUNT OF DEPOSITED COKE[wt%] | 3.4 | 4.8 | 8.2 |

[Fig 5]
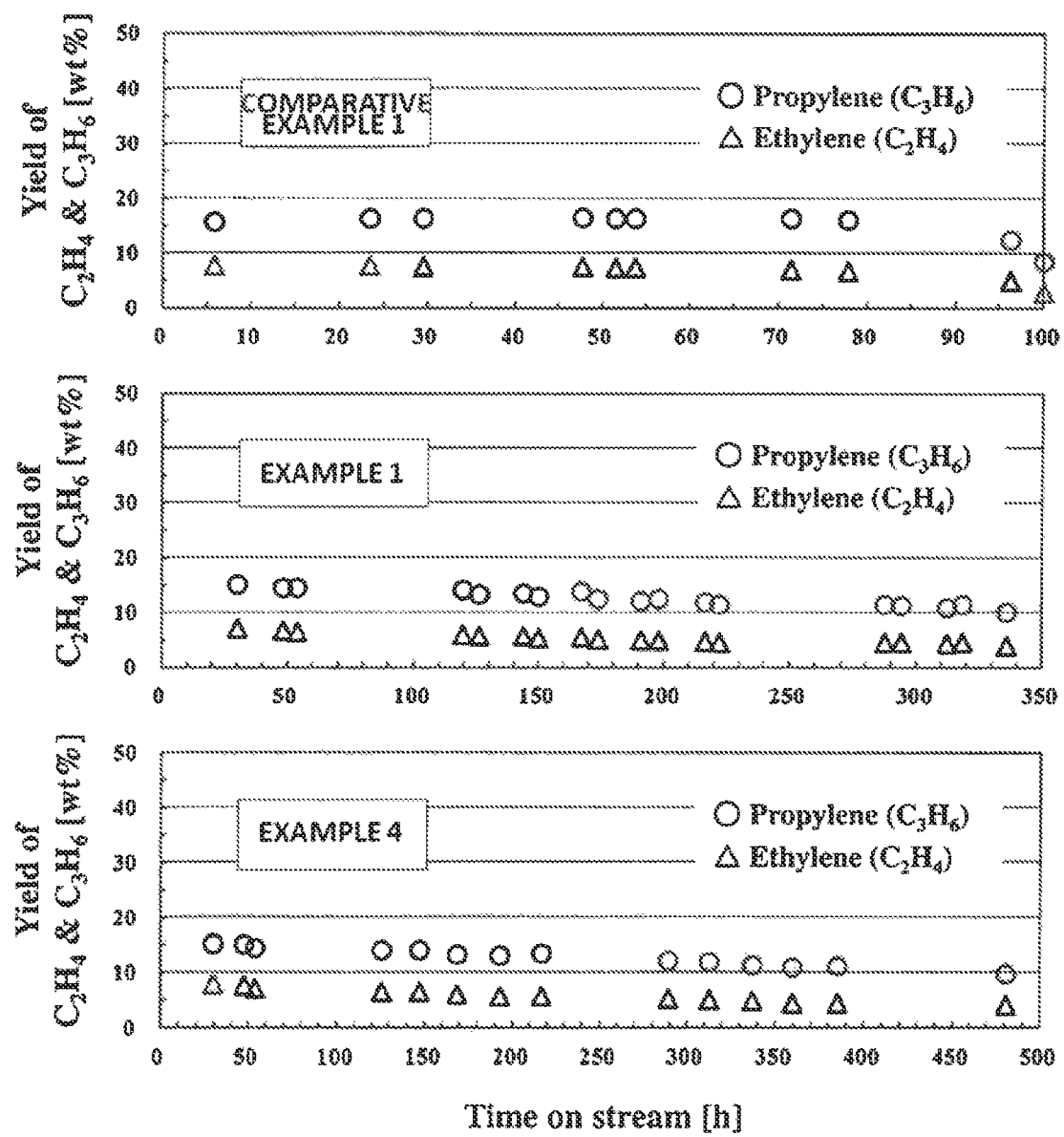

[Fig. 6]

|  | EXAMPLE 4 | EXAMPLE 5 | EXAMPLE 6 | COMPARATIVE EXAMPLE 2 |
|---|---|---|---|---|
| COMPOSITE OF ZEOLITE/METAL OXIDE | FeGaAl-MFI / SiO$_2$ | FeGaAl-MFI / SiO$_2$ | FeGaAl-MFI / SiO$_2$ | FeGaAl-MFI / SiO$_2$ |
| ACID DENSITY OF ZEOLITE (Si/(Fe+Ga+Al))[mol/mol] | 121.3 | 121.3 | 121.3 | 121.3 |
| MIXED RATIO OF ZEOLITE/BINDER[wt%/wt%] | 90 / 10 | 90 / 10 | 90 / 10 | 90 / 10 |
| REACTION TEMPERATURE [°C] /PRESSURE[MPa] | 565 / 0.1 | 565 / 0.1 | 565 / 0.1 | 565 / 0.1 |
| AMOUNT OF CHARGED CATALYST[mL] | 2.0 | 2.0 | 2.0 | 2.0 |
| LHSV OF n-HEXANE[h$^{-1}$] | 4.5 | 6.0 | 7.0 | 15.0 |
| CONTACT TIME(=1/LHSV)[h] | 0.23 | 0.17 | 0.14 | 0.07 |
| INITIAL n-HEXANE CONVERSION[wt%] | 68.7 | 60.4 | 59.3 | 41.0 |
| INITIAL ETHYLENE YIELD[wt%] | 8.0 | 6.8 | 6.4 | 4.1 |
| INITIAL PROPYLENE YIELD[wt%] | 15.6 | 15.2 | 15.1 | 10.7 |
| INITIAL YIELD OF AROMATIC HYDROCARBONS[wt%] | 4.6 | 2.8 | 2.2 | 0.75 |

[Fig. 7]

|  | EXAMPLE 5 | EXAMPLE 7 | EXAMPLE 8 |
|---|---|---|---|
| COMPOSITE OF ZEOLITE/METAL OXIDE | FeGaAl-MFI / SiO$_2$ | FeGaAl-MFI / SiO$_2$ | FeGaAl-MFI / SiO$_2$ |
| ACID DENSITY OF ZEOLITE (Si/(Fe+Ga+Al))[mol/mol] | 121.3 | 121.3 | 121.3 |
| MIXED RATIO OF ZEOLITE/BINDER[wt%/wt%] | 90 / 10 | 90 / 10 | 90 / 10 |
| REACTION TEMPERATURE [°C] | 565 | 585 | 635 |
| PRESSURE[MPa] | 0.1 | 0.1 | 0.1 |
| AMOUNT OF CHARGED CATALYST[mL] | 2.0 | 2.0 | 2.0 |
| LHSV OF n-HEXANE[h$^{-1}$] | 6.0 | 6.0 | 6.0 |
| INITIAL n-HEXANE CONVERSION[wt%] | 60.4 | 60.8 | 89.8 |
| INITIAL ETHYLENE YIELD[wt%] | 6.8 | 7.3 | 13.3 |
| INITIAL PROPYLENE YIELD[wt%] | 15.2 | 16.3 | 20.5 |
| INITIAL YIELD OF AROMATIC HYDROCARBONS[wt%] | 2.8 | 3.3 | 6.5 |

[Fig. 8]
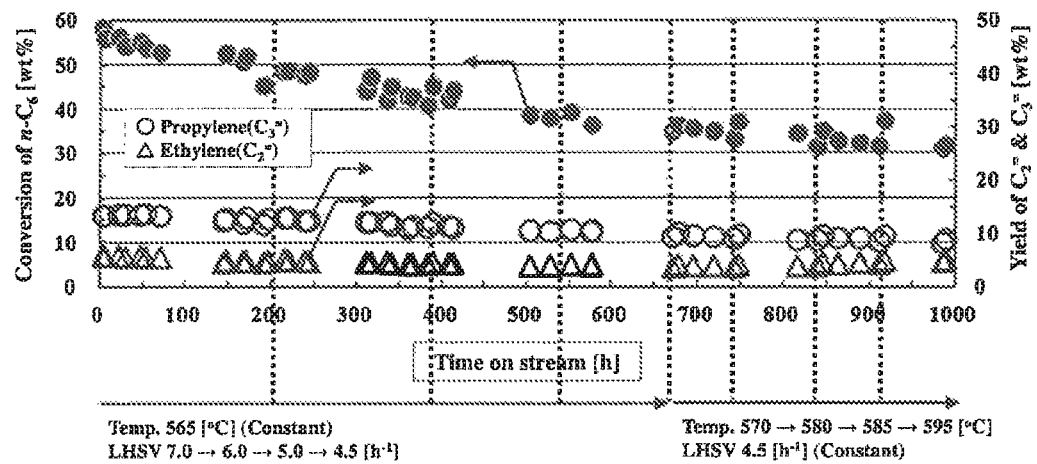
[Fig. 9]
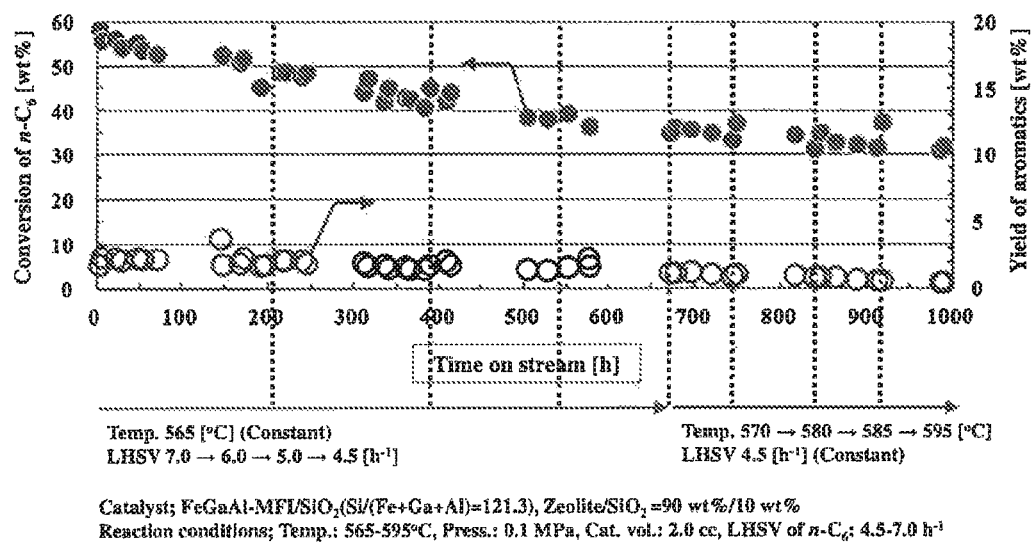

[Fig. 10]
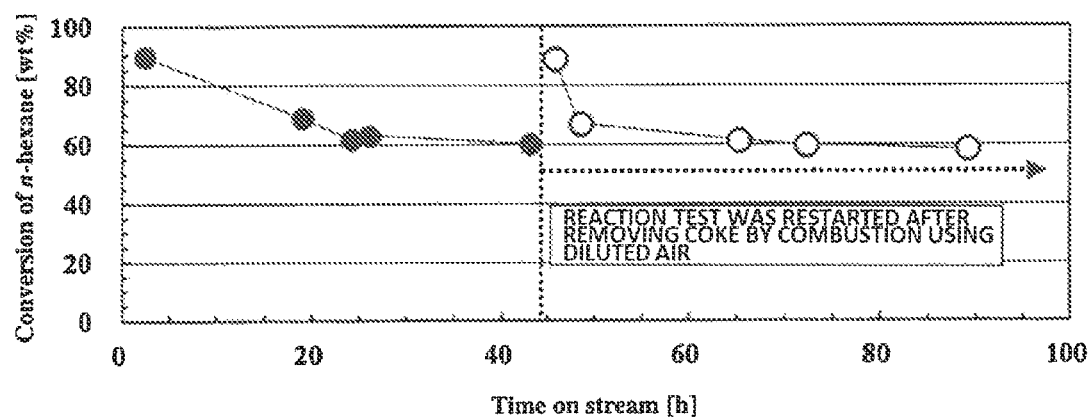
Catalyst; FeGaAl-MFI*/SiO$_2$, Zeolite/SiO$_2$=65 wt%/35 wt%
*Si/(Fe+Ga+Al)=31.3, Fe/(Fe+Ga+Al)=0.4, Ga/(Fe+Ga+Al)=0.3, Al/(Fe+Ga+Al)=0.3
Reaction conditions; Temperature: 565°C, Pressure: 0.1 MPa, Catalyst volume: 2.0 cc, LHSV of $n$-C$_6$: 4.5 h$^{-1}$

COMPOSITE CATALYST, METHOD FOR PRODUCING COMPOSITE CATALYST, METHOD FOR PRODUCING LOWER OLEFIN AND METHOD FOR REGENERATING COMPOSITE CATALYST

TECHNICAL FIELD

The present invention relates to a composite catalyst for the production of a lower olefin used in the production of a lower olefin from a hydrocarbon feedstock, a method for producing the composite catalyst, a method for producing a lower olefin by using the composite catalyst, and a method for regenerating a composite catalyst in the method for producing a lower olefin.

BACKGROUND ART

A lower olefin (ethylene or propylene) that is an important basic feedstock in petrochemistry is expected to grow in the demand at a steady pace also in the future. Currently, 60% of propylene has been produced by a steam cracking process (steam cracker) of naphtha or the like. However, this technique requires a high temperature of 800 to 900° C. for decomposition because of the absence of a catalyst, and is an energy-intensive process by charging excessive steam.

In addition, the main product of the above-described technique is ethylene, and propylene is produced as a by-product, therefore, in a case where naphtha is used as a feedstock, the production ratio is approximately fixed as ethylene/propylene=2/1. There is a possibility of having a situation that the supply of propylene may not catch up with the expanding demand for propylene in the future. From the viewpoint described above, an alternative process for efficiently producing propylene from a naphtha feeds tock with as little energy consumption as possible is strongly desired.

Currently, as an alternative method of a steam cracker, an energy-saving method for producing propylene, to which a fixed bed-type naphtha catalytic cracking method using a zeolite catalyst is applied, has been researched and developed.

For example, it has been proposed that a crystalline aluminosilicate having a MFI-type structure containing iron or iron and gallium is used as a catalyst when a lower olefin is produced from a low-boiling hydrocarbon feedstock such as light naphtha (see for example, Patent Literatures 1 to 3).

According to the zeolite catalyst described in these Patent Literatures 1 to 3, with a relatively low reaction temperature, the production amount of the propylene relative to the ethylene can be increased, and further the catalyst lifetime can be extended.

CITATION LIST

Patent Literatures

Patent Literature 1: JP 2014-24005 A
Patent Literature 2: JP 2014-24006 A
Patent Literature 3: JP 2014-24007 A

SUMMARY OF INVENTION

Technical Problem

By the way, in practical application of the production of a lower olefin using a zeolite catalyst, it is desired that a fixed bed system at an equipment cost lower than that of a fluidized bed system is used. In this case, it is preferred that a lower olefin can be produced stably and continuously over a long period of time by using a fixedly arranged zeolite catalyst, and it is required that a zeolite catalyst has further longer lifetime.

Herein, as a factor shortening the lifetime of a zeolite catalyst, pore clogging accompanying the carbon deposition, that is, coke generation (coking) can be mentioned. In the generation of coke, aromatic hydrocarbon generated as a by-product by catalytic action of a zeolite catalyst is a big factor. Herein, a zeolite catalyst has an acid point as a solid acid, and at this acid point a hydrocarbon molecule to be a feedstock is decomposed and further dehydrogenated to generate a lower olefin, however, when the generated olefin remains at the acid point without leaving the acid point, the reaction further proceeds by catalytic action, and aromatic hydrocarbon is generated by a cyclization and dehydrogenation reaction. Coke is generated from the aromatic hydrocarbon, and the catalytic activity of a zeolite catalyst is lowered as described above.

The present invention has been made in view of such a circumstance, and an object of the present invention is to provide a composite catalyst capable of further extending the lifetime of a catalyst in the production of a lower olefin by using a zeolite catalyst, a method for producing the composite catalyst, a method for producing a lower olefin by using the composite catalyst, and a method for regenerating a composite catalyst in the method for producing a lower olefin.

Solution to Problem

To achieve the above object, a composite catalyst of the present invention is a composite catalyst for producing a lower olefin from a hydrocarbon feedstock, including:

a zeolite being a crystalline aluminosilicate containing gallium and iron or iron and further having a framework with 8- to 12-membered ring; and silicon dioxide.

According to such a constitution, in a composite catalyst including a zeolite that is a crystalline aluminosilicate containing iron or iron and gallium, and silicon dioxide, by making a zeolite having catalytic action, and silicon dioxide as a binding agent (binder) into a composite, the generation amount of coke is reduced by suppressing the generation of aromatic hydrocarbon while suppressing the reduction of the production amount of ethylene and propylene, as a result of which the lifetime of a composite catalyst can be further extended.

In addition, in Patent Literatures 1 to 3, aluminum oxide (alumina powder) is used as a binding agent. However, the present inventors have found that the catalyst lifetime is apparently extended by using silicon dioxide (silica) as a binding agent. That is, the present inventors have found that the catalyst lifetime can be extended by mixing silicon dioxide with the above-described zeolite. This can be considered that due to the effect of the silicon dioxide that is coexisted in at least part of the acid point existing on an outer surface of a zeolite, for example, the generation of the aromatic hydrocarbon from a lower olefin is suppressed on an outer surface of a zeolite by the decrease of the acid strength at the acid point, and the generation of coke is inhibited. Accordingly, a lower olefin can be sufficiently and efficiently produced over a long period of time, and the production of a lower olefin from a hydrocarbon feedstock can be realized with a fixed bed system.

In the above constitution of the present invention, it is preferable that the zeolite is a crystalline aluminosilicate containing iron and gallium, and an acid density as a composition ratio of the number of moles of silicon to a sum of the number of moles of iron, gallium, and aluminum is 75.0 to 200.0, a composition ratio of the number of moles of gallium to a sum of the number of moles of iron, gallium, and aluminum is 0.1 to 0.4, and a composition ratio of the number of moles of iron to a sum of the number of moles of iron, gallium, and aluminum is 0.2 to 0.6.

According to such a constitution, by setting each of the acid density, the molar composition ratio of iron (Fe), and the molar composition ratio of gallium (Ga) in the above-described range, the production amount of the propylene relative to the ethylene can be further increased, and further the generation of aromatic hydrocarbon can be further suppressed under the coexistence of silicon dioxide that is a binding agent. Herein, in iron, there is a function for suppressing the acid strength at the acid point of a zeolite, and in gallium, there is a function for promoting a dehydrogenation reaction of an alkane.

Further, in the above-described constitution of the present invention, it is preferable that the zeolite is a crystalline aluminosilicate containing iron, and an acid density as a composition ratio of the number of moles of silicon to a sum of the number of moles of iron, and aluminum is 75.0 to 200.0, and a composition ratio of the number of moles of iron to a sum of the number of moles of iron, and aluminum is 0.4 to 0.7.

According to such a constitution, by setting each of the acid density, the molar composition ratio of iron, and the molar composition ratio of gallium in the above-described range, the production amount of the propylene relative to the ethylene can be further increased, and further the suppressive effect of the generation of aromatic hydrocarbon can be further increased under the coexistence of silicon dioxide that is a binding agent.

In addition, in the above-described constitution of the present invention, a concentration of the silicon dioxide is preferably 5 to 50 wt %, and more preferably 5 to 40 wt %.

According to such a constitution, the generation amount of aromatic hydrocarbon can be more efficiently reduced while suppressing the reduction of the production amount of propylene. As a result, the lifetime of the catalytic function in a zeolite of a composite catalyst can be more effectively extended.

A method for producing the composite catalyst according to the present invention, including:

a hydrothermal synthesis process, a molding process, and an ion exchange process.

According to such a constitution, in a hydrothermal synthesis process performed in the presence of water at a high temperature and a high pressure, a zeolite component in the composite catalyst of the present invention, which is a crystalline aluminosilicate containing iron or iron and gallium, is synthesized from, as a feedstock, a silica source, an alumina source, an iron source or an iron source and a gallium source, a mineralizer, and water.

In addition, in a molding process, silicon dioxide as a binding agent is added into the zeolite synthesized in the hydrothermal synthesis process, and the resultant mixture is kneaded, formed, dried, fired, and the like to produce a composite catalyst in a predetermined shape. By the silicon dioxide as a binding agent used at this time, the generation of aromatic hydrocarbon can be suppressed as described above. Further, in an ion exchange process, by introducing an acidic OH group, the zeolite is allowed to exhibit a property as solid acid.

In addition, as to the process order in the production of a composite catalyst, for example, the molding process can be performed after the ion exchange process, but the production is preferably performed in the order of the hydrothermal synthesis process, the molding process, and the ion exchange process. The workability is improved in performing the ion exchange process to the composite catalyst molded into a predetermined shape rather than in performing the ion exchange process to the powdery zeolite obtained in the hydrothermal synthesis process. Further, when a composite catalyst is molded using silicon dioxide as a binding agent, and then the acid point is allowed to exhibit by an ion exchange process, there is a possibility that the generation of aromatic hydrocarbon can be suppressed.

In the above-described constitution of the present invention, in the molding process described above, it is preferred that an alkaline aqueous solution containing starch as a molding aid is used in molding a mixture of a zeolite and silicon dioxide.

According to such a constitution, in the molding process, with a thickening property obtained by adding an alkaline aqueous solution that contains starch when a zeolite and silicon dioxide are kneaded, a mixture in a massive state is easily obtained.

A method for producing a lower olefin, in which a lower olefin is produced from a hydrocarbon feedstock by using the composite catalyst of the above-described constitution of the present invention, the method is characterized in that a gas containing 15 wt % or more, and more preferably 50 wt % or more of the hydrocarbon feedstock is supplied to the composite catalyst, and a reaction of producing the lower olefin from the hydrocarbon feedstock is allowed to progress in a temperature range of 530° C. to 650° C., and more preferably in a temperature range of 550° C. to 640° C.

According to such a constitution, as compared with a steam cracking process, the reaction temperature is low, the energy efficiency is excellent, and the cost can be reduced. Further, by producing a lower olefin at a relatively low temperature, the generation of aromatic hydrocarbon is suppressed, and the lifetime of a composite catalyst can be extended.

In addition, the reaction can be performed while adjusting the temperature in a temperature range of 530° C. to 650° C. In the present invention, a composite catalyst can be used over a long period of time, but the production amount of a lower olefin is gradually decreased due to the deterioration of a catalyst with the lapse of time. Accordingly, for example, by gradually increasing the reaction temperature with the lapse of time, the production amount of a lower olefin can be stabilized over a long period of time, and the replacement time and regeneration time of a composite catalyst can be postponed.

In addition, a method for producing a lower olefin, in which a lower olefin is produced from a hydrocarbon feedstock by using the composite catalyst of the above-described constitution of the present invention, and in which a gas containing 15 wt % or more, and more preferably 50 wt % or more of the hydrocarbon feedstock is supplied to the composite catalyst, and the contact time of the hydrocarbon feedstock with the composite catalyst is preferably 0.08 to 1.0 h, and more preferably 0.08 to 0.4 h.

According to such a constitution, by setting the contact time of the hydrocarbon feedstock with the composite catalyst in a range of 0.08 to 1.0 h, and more preferably 0.08 to 0.4 h, a lower olefin can be more efficiently produced, and further the generation amount of aromatic hydrocarbon is suppressed and the lifetime of the composite catalyst can be extended. That is, as the contact time becomes shorter, the production amount of a lower olefin is decreased and the generation amount of aromatic hydrocarbon is also decreased, and the lifetime of the composite catalyst becomes longer, and as the contact time becomes longer, the production amount of a lower olefin is increased and the generation amount of aromatic hydrocarbon is also increased, and the lifetime of the composite catalyst becomes shorter. Therefore, it is preferred that the contact time is set by taking into consideration the production amount of a lower olefin and the lifetime of a composite catalyst.

In addition, in the present invention, a composite catalyst can be used over a long period of time, but the production amount of a lower olefin is gradually decreased due to the deterioration of a catalyst with the lapse of time. Accordingly, for example, by gradually increasing the contact time of the feedstock with the composite catalyst with the lapse of time, the production amount of a lower olefin can be stabilized over a long period of time, and the replacement time and regeneration time of a composite catalyst can be postponed.

A method for regenerating a composite catalyst, in which deposited carbon is burned and removed from the composite catalyst used in the method for producing a lower olefin of the above-described constitution of the present invention, the method is characterized in that air diluted with inert gas is supplied to the composite catalyst, and the deposited carbon is burned and removed in a temperature range of 450° C. to 600° C., and more preferably 500° C. to 550° C.

According to such a constitution, a composite catalyst can be used without replacing the composite catalyst, and the period of use of a composite catalyst can be further extended, therefore, the reduction of cost can be achieved. In addition, the temperature for burning and removing deposited carbon is lower than the reaction temperature at the time of producing a lower olefin or is the same level as the reaction temperature, therefore, the temperature is a temperature usable in a production facility of a lower olefin without causing any problems, accordingly improvement of the heat resistance, enhancement of a heating equipment, and the like are not required for the regeneration, and the regeneration can be performed without increasing the equipment cost.

Advantageous Effects of Invention

According to the present invention, by mixing silicon dioxide as a binding agent into a zeolite that is a crystalline aluminosilicate containing iron or iron and gallium, and by molding the resultant mixture into a shape, the deterioration of a catalytic function of the zeolite is suppressed and the catalyst lifetime can be extended in the production of a lower olefin using a catalyst.

BRIEF DESCRIPTION OF DRAWINGS

FIG. 1 is a drawing for explaining a composition of each composite catalyst of Examples 1 and 2, and Comparative Example 1 in the present invention.

FIG. 2 is a drawing for explaining performance comparison of each composite catalyst of Examples 1 and 2, and Comparative Example 1.

FIG. 3 is a drawing for explaining a composition with a different content of silicon dioxide in each composite catalyst of Examples 1, 3, and 4.

FIG. 4 is a drawing for explaining performance comparison of each composite catalyst of Examples 1, 3, and 4.

FIG. 5 is a graph showing changes over time of the yield of a lower olefin in a reaction test using each composite catalyst of Examples 1 and 4, and Comparative Example 1.

FIG. 6 is a drawing showing a relationship between the contact time and the initial performance of a composite catalyst in each of Examples 4, 5, and 6, and Comparative Example 3 as a reaction test in which the contact time of a feedstock with a composite catalyst is different from each other by using the similar composite catalyst to that in Example 4.

FIG. 7 is a drawing showing a relationship between the reaction temperature and the initial performance of a composite catalyst in each of Examples 5, 7, and 8, as a reaction test in which the reaction temperature is different from each other by using the similar composite catalyst to that in Example 4.

FIG. 8 is a graph showing the results of along-term reaction test as Example 9 by using the similar composite catalyst to that in Example 4.

FIG. 9 is a graph showing the results of along-term reaction test as Example 9.

FIG. 10 is a graph showing the results of a regeneration test of a composite catalyst as Example 10.

DESCRIPTION OF EMBODIMENTS

Hereinafter, the embodiment of the present invention will be described.

In this embodiment, a composite catalyst for efficiently producing a lower olefin such as propylene over a long period of time, a method for producing the composite catalyst, a method for producing a lower olefin by using the composite catalyst, and a method for regenerating the composite catalyst in the method for producing a lower olefin will be described.

The composite catalyst of the present embodiment is a composite including a zeolite that is a crystalline aluminosilicate containing gallium and iron or iron and further having a framework with 8- to 12-membered ring, and silicon dioxide that functions as a binding agent for molding.

Herein, the zeolite that is a crystalline aluminosilicate has a framework with 8- to 12-membered ring. The skeleton structure of a zeolite is stored in a database by International Zeolite Association, and given a structure code consisting of three alphabet capital letters. This structure code specifies only the geometric structure of the skeleton.

For example, there is LTA or the like as a structure code of a framework with 8-membered ring, there is FER, MWW, MFI or the like as a structure code of a framework with 10-membered ring, and there is MOR, LTL, FAU, BEA or the like as a structure code of a framework with 12-membered ring. In addition, herein, only some structure codes of a zeolite having each membered ring are indicated. The diameter of pores of a zeolite is affected by the number of membered ring of a framework, and the diameter of pores is defined to some extent by having an 8- to 12-membered ring. For example, in the whole zeolite, the pore diameter is around 0.2 to 1.0 nm, and in a case of a zeolite having a framework with 8- to 12-membered ring, the pore diameter is around 0.40 nm to 0.75 nm. In the present embodiment, as to the size of pores of a zeolite, a zeolite that is suitably used when propylene (ethylene) is produced by utilizing the catalytic function of a zeolite by using, for example, a C4 to C8 lower olefin as a hydrocarbon feedstock is preferred, and for example, the size of pores is preferably around 0.40 nm to 0.75 nm as described above, but the size is not limited in this range.

In this case, the number of membered ring of a framework of a zeolite is preferably 8 to 12 as described above, and the number of membered ring is more preferably 10 to 12. In addition, for example, as an MFI-type zeolite having a framework with 10-membered ring, ZSM-5 (Zeolite Socony Mobil-5) is known, and as a BEA-type zeolite having a framework with 12-membered ring, a beta-type zeolite is known. As described above, as to the zeolite of the present embodiment, an MFI-type zeolite or a beta-type zeolite can be suitably used as an 8- to 12-membered ring zeolite. In particular, an MFI-type zeolite can be suitably used.

In addition, in the present embodiment, as a zeolite, for example, a crystalline aluminosilicate containing an iron (Fe) element and a gallium (Ga) element or an iron element is used. Further, Fe has a function for suppressing the acid strength at the acid point of a zeolite. Furthermore, Ga has a function for promoting a dehydrogenation reaction of an alkane. The zeolite catalyst of the present embodiment is a composite catalyst obtained by the molding with the addition of a binding agent (binder) and the firing, and silicon dioxide is used as the binder.

In a zeolite that is an MFI-type crystalline aluminosilicate containing an iron element (without containing any gallium elements), the elemental molar composition ratio of iron element (iron element/(iron element+aluminum element (Al))) is preferably 0.4 to 0.7, and more preferably 0.4 to 0.6.

In addition, in a zeolite that is an MFI-type crystalline aluminosilicate containing an iron element (without containing any gallium elements), the acid density (silicon element (Si)/(iron element+aluminum element) element ratio) is preferably 75.0 to 200.0, and more preferably 80.0 to 200.0. Further, the element ratio means a composition ratio by the number of moles of each of the elements described above.

In addition, in a zeolite that is an MFI-type crystalline aluminosilicate containing an iron element and a gallium element, the elemental molar composition ratio of iron element (iron element/(iron element+gallium element+aluminum element)) is preferably 0.2 to 0.6, and more preferably 0.3 to 0.5.

In addition, in a zeolite that is an MFI-type crystalline aluminosilicate containing an iron element and a gallium element, the elemental molar composition ratio of gallium element (gallium element/(iron element+gallium element+aluminum element)) is preferably 0.1 to 0.4, and more preferably 0.2 to 0.4.

In addition, in an MFI-type zeolite catalyst containing an iron element and a gallium element, the acid density (silicon element/(iron element+gallium element+aluminum element) element ratio) is preferably 75.0 to 200.0, and more preferably 80.0 to 200.0.

As described above, by using a zeolite of this embodiment, which is an MFI-type crystalline aluminosilicate containing an iron element, the acid strength can be adjusted from the content of iron element and the acid density, and further, by the addition of a gallium element, the promoting action of the dehydrogenation of an alkane can be improved. At the acid point of a zeolite, the alkane is divided, and further a double bond of carbon is generated by a decarburization reaction, and a lower olefin is produced, but for example, when the acid strength at the acid point is extremely strong, the reaction further proceeds even after the lower olefin has been produced without the lower olefin leaving from the acid point, and aromatic hydrocarbon is generated by a cyclization and dehydrogenation reaction. As the generation amount of aromatic hydrocarbon is increased, the deposition amount of coke is increased, and as a result of which the lifetime of the composite catalyst is shortened. Accordingly, in reducing the deposition amount of coke, the adjustment of the acid strength is important.

By setting the composition ratio of the number of moles of iron element, the composition ratio of the number of moles of gallium element, and the acid density in the ranges described above, the yield of propylene can be improved, and further the generation of aromatic carbon, which causes coke generation, can be suppressed.

In addition, the content of silicon dioxide (silica) as a binding agent in a composite catalyst relative to the composite catalyst is preferably 5 to 50 wt % (% by weight), and more preferably 5 to 40 wt %. In increasing the yield of a lower olefin, it is preferred to decrease the content of silicon dioxide and to increase the content of a zeolite, and in suppressing the generation of aromatic hydrocarbon, it is preferred to increase the content of silicon dioxide. In addition, it is presumed that the action to cover and inactivate the acid point on an outer surface of a zeolite is stronger in silicon dioxide as a binding agent than in aluminum oxide (alumina) as a binding agent.

Accordingly, by covering and inactivating the acid point on an outer surface of a zeolite, the generation of aromatic hydrocarbon at the acid point on an outer surface of a zeolite is suppressed, and further the carbon deposition on an outer surface of a zeolite is suppressed, and it is considered that the catalytic activity to convert an alkane to a lower olefin inside the pores of a zeolite can be maintained for a long period of time. Such an action mechanism effectively acts on a zeolite that has definite catalytic action to the reaction of producing a lower olefin from an alkane, for example, a zeolite that is a crystalline aluminosilicate containing gallium and iron or iron and further having a framework with 8- to 12-membered ring, and further that functions as a catalyst for producing a lower olefin from a hydrocarbon feedstock.

The zeolite as such a solid acid catalyst (zeolite catalyst) is produced through the processes that are roughly classified into three: 1. Hydrothermal synthesis process, 2. Molding process, and 3. Ion exchange process.

1. Hydrothermal Synthesis Process

The "hydrothermal synthesis method" is a generic term for a synthetic method of a substance, which is performed in the presence of water at a high temperature and a high pressure, and many of the zeolites as a crystalline aluminosilicate are synthesized by this hydrothermal synthesis method. As a feedstock to be used for the synthesis, a silica source (such as sodium silicate, colloidal silica, and fumed silica), an alumina source (such as aluminum hydroxide, and sodium aluminate), a structure directing agent (such as amine), a mineralizer (such as a hydroxide of an alkali metal), water, or the like is generally used.

In the zeolite of this embodiment, an iron source (for example, iron nitrate, iron oxide, iron sulfate, iron phosphate, iron chloride, iron bromide, metal iron (iron powder), organic acid iron, or the like) is added in the feedstock, and further, a gallium source (for example, gallium nitrate, gallium oxide, gallium sulfate, gallium phosphate, gallium chloride, gallium bromide, gallium hydroxide, or the like) is preferably added in the feedstock. These are mixed, and an amorphous hydrogel (mother gel) having high reactivity is prepared and filled in an autoclave that is a pressure resistant reactor, and then the amorphous hydrogel is heated at around 150° C. for a predetermined time to synthesize a zeolite. After the hydrothermal synthesis reaction, a powdery zeolite is obtained through the steps of separation of product, water washing, drying, firing (performed in order to decompose and remove the structure directing agent) and the like.

The more detailed description of the method for producing a zeolite is as follows. A mother liquor gel A including colloidal silica having a particle size of 8 to 11 nm as fine silica that is a silicon source and sodium hydroxide (NaOH) for the pH adjustment, and a mother liquor gel B containing $Al_2(SO_4)$-$nH_2O$ as an aluminum source, $Ga(NO_3)_3$-$nH_2O$ as a gallium source, $Fe(NO_3)_3$-$nH_2O$ as an iron source, and tetrapropylammonium bromide (TPrABr) as a structure directing agent are prepared. In addition, it is preferred that the additive amount of TPrABr as a structure directing agent is reduced.

Next, these mother liquor gel A and mother liquor gel B are stirred and mixed (for example, for 15 minutes). As a result, an amorphous hydrogel having high reactivity is prepared. Subsequently, the stirred and mixed mother liquor gel is aged (for example, at 60° C. overnight). Next, in the above-described hydrothermal synthesis, the aged mother liquor gel is stirred at 120° C. to 150° C. with a rotational speed of 150 rpm to 300 rpm (for example, performing the hydrothermal synthesis in an autoclave under self-pressure). That is, the crystallization is performed under a high temperature and a high pressure. However, as the reaction temperature, the temperature is relatively low, accordingly the nucleus is grown at a low temperature, and the generation of coarse particles is suppressed. In addition, as the stirring speed, the speed is relatively high speed, and the nuclei are generated in a large amount. The stirring is performed under the conditions, for example, for 24 hours to obtain crystals. The obtained crystals are washed with water, and the dehydration is performed by centrifugation. After that, the crystals are dried, for example, at 120° C. for 3 hours, and further fired at 550° C. for 3 hours to remove the TPrABr. Further, in a case of containing no gallium, a gallium source is not added into the mother liquor gel B.

2. Molding Process

In general, in a case where a zeolite is industrially used as a catalyst, from the viewpoint of the improvement of mechanical properties or the reduction of pressure loss, the zeolite is used in many cases by being molded into a cylindrical shape or the like. The present process includes steps of kneading of mainly the zeolite synthesized as described above with silicon dioxide that is a binding agent (binder), molding, drying, firing, and the like. Further, in the molding, for example, an extrusion molding method or the like is used.

For example, into the powdery zeolite obtained through the above-described hydrothermal synthesis process (or the ion exchange process), silica powder, and starch as a molding aid are mixed, and then into the resultant mixture, an aqueous sodium hydroxide solution (alkaline aqueous solution) is added and kneaded, and a mixture in a massive state is obtained. In addition, as the molding aid, it is not limited to starch, for example, a molding aid may be used, which has a viscosity increasing when water is added, can make a mixture of a zeolite powder and silica powder into a massive state when the zeolite powder and the silica powder are kneaded with water, and approximately all of which becomes, for example, water and carbon dioxide during firing and disappears from the molded body, and for example, a PVP (polyvinyl pyrrolidone) or the like may be used.

This mixture is processed into a cylindrical shape, for example, by extrusion molding, and dried at 120° C. for around 3 hours. Next, the resultant product is fired at 550° C. for 3 hours under air circulation, and the composite catalyst of the present embodiment can be obtained.

In addition, the molding process may be performed after the ion exchange process, or the ion exchange process may also be performed after the molding process, and it is preferred that the ion exchange process is performed after the molding process.

3. Ion Exchange Process

In many of the chemical reactions utilizing a zeolite as a catalyst, the property as the solid acid is utilized, and the property as the acid is developed by introducing an acidic OH group (Bronsted acid site) into a zeolite.

In order to develop the acid property, in general, an ion exchange reaction is applied. Usually, the zeolite obtained by a hydrothermal synthesis method contains a sodium cation ($Na^+$) in order to maintain the balance of electric charges, and the sodium cation is subjected to ion exchange to be replaced with a proton ($H^+$). In addition, a method in which once ion exchange is performed with an ammonium ion ($NH_4^+$) by an $NH_4NO_3$ solution, and further the ammonia is removed by drying and firing to convert to a proton ($H^+$) may also be used. For example, the process of ion exchange by an aqueous ammonium nitrate solution under boiling reflux followed by water washing is repeated four times, and then through the drying at 120° C. for 3 hours and the firing at 550° C. for 3 hours under air circulation, a proton-type composite catalyst can be obtained.

In a case where the ion exchange process is performed after the molding process, in the production of a lower olefin by using the zeolite catalyst, there is a possibility that the generation of aromatic hydrocarbon that causes coke generation can be suppressed. In addition, as compared with the powdery crystalline aluminosilicate of the hydrothermal synthesis process, a zeolite catalyst molded after the molding process is more easily handled, and the workability can be improved in the ion exchange process.

In a production method in which by using such a composite catalyst, a lower olefin is produced from, for example, light naphtha, the feedstock gas such as light naphtha or the like is supplied to a reactor without being diluted with inert gas such as nitrogen or a diluent such as water vapor. That is, the reaction is performed by bringing a hydrocarbon feedstock into contact with a composite catalyst. Further, a diluent may also be contained in the feedstock gas, and in this case, in the gas to be supplied to a composite catalyst, a hydrocarbon material such as light naphtha is contained preferably in an amount of 15 wt % or more, and more preferably in an amount of 50 wt % or more. A method in which the above-described composite catalyst is placed in a reactor as a fixed bed, and the feedstock gas to be supplied into the reactor is allowed to pass through while being brought into contact with the composite catalyst is used. In this case, the reaction is allowed to proceed in a mild temperature range of 530° C. to 650° C., and more preferably 550° C. to 640° C., and ethylene and propylene are produced.

In addition, the hydrocarbon feedstock of a lower olefin is, for example, a low-boiling hydrocarbon feedstock such as light naphtha, and naphtha (full range naphtha) means a product having a boiling point range of roughly around 30 to 200° C. among the products obtained by distilling crude oil with an atmospheric distillation apparatus. As to naphtha, the naphtha having a boiling point range of around 30 to 100° C. is referred to as light naphtha, and the naphtha having a boiling point range of around 100 to 200° C. is referred to as heavy naphtha. Further, light naphtha is equivalent to the fraction that contains pentane having 5 carbon atoms and hexane having 6 carbon atoms as the main components.

In addition, the low-boiling hydrocarbon feedstock is basically light naphtha, but may contain, for example, partially heavy naphtha, or may be full range naphtha. Further, the low-boiling hydrocarbon feedstock may also be a material other than naphtha, and is, for example, natural gas other than oil, or other hydrocarbon feedstocks, basically a fraction equivalent to light naphtha can be used. Furthermore, a by-product or the like at the time of producing various kinds of products from oil or natural gas can also be utilized as a hydrocarbon feedstock, the hydrocarbon basically having a boiling point not so high can be used as a feedstock. Moreover, in the present embodiment, there may be a case where the lower olefin is defined to contain as an olefin having less carbon atoms, for example, ethylene, propylene, butene, or an olefin having more carbon atoms than those of butene (for example, 5 to 8 carbon atoms or the like), but herein, the lower olefin includes at least ethylene having 2 carbon atoms, and propylene having 3 carbon atoms.

In addition, in the reaction of producing a lower olefin, the contact time as the reciprocal of a liquid hourly space velocity (LHSV) of a feedstock hydrocarbon in the composite catalyst of the present embodiment is preferably set to 0.08 to 1.0 h, and more preferably 0.08 to 0.4 h. The LHSV is preferably set to 1.0 to 12.5 $h^{-1}$, and more preferably set to 2.5 to 12.5 $h^{-1}$. Herein, the term "LHSV" is referred to as the speed at the time of supplying a feedstock hydrocarbon as a liquid to a composite catalyst, and the term "contact time" is referred to as the time when a feedstock hydrocarbon passes through a composite catalyst (as described above, the feedstock is in a gas state from a liquid state when the feedstock is supplied to a composite catalyst, but herein, the space velocity of the feedstock in a liquid state before gasifying to be supplied to a reaction vessel is used). Further, as the space velocity, a space velocity (GHSV) of feedstock gas may be used, or a space velocity (WHSV) of weight may also be used.

In the production of a lower olefin, as the reaction temperature is higher, the conversion rate of a hydrocarbon feedstock becomes higher, and as the production amount of a lower olefin becomes larger, the generation amount of aromatic hydrocarbon becomes larger, therefore, the reaction temperature is required to be determined with a balance among the energy efficiency at the time of heating, the production amount of a lower olefin, and the lifetime of a composite catalyst by the increase in aromatic hydrocarbon. By setting to the range described above, the long lifetime of a composite catalyst is ensured, and further the stable production of a lower olefin can be ensured.

Further, in the production of a lower olefin, as the contact time is longer, the conversion rate of a hydrocarbon feedstock becomes higher, and as the production amount of a lower olefin becomes larger, the generation amount of aromatic hydrocarbon becomes larger, therefore, the contact time is required to be determined with a balance between the production amount of a lower olefin, and the lifetime of a composite catalyst by the increase in aromatic hydrocarbon. By setting to the range described above, the long lifetime of a composite catalyst is ensured, and further the stable production of a lower olefin can be ensured.

Herein, in a case where the composite catalyst of the present embodiment is continuously used, the generation amount of aromatic hydrocarbon becomes smaller as compared with the conventional ones, and as a result of which the amount of deposited carbon also becomes smaller, therefore, the lifetime of a composite catalyst is extended. In the production of a lower olefin for a long time, for example, in a case where the yield of a lower olefin is decreased until the value set to be the lowest limit, when the replacement or regeneration of a composite is performed, the yield of a lower olefin gradually decreases with the lapse of time. Accordingly, corresponding to the lapse of time, by increasing the reaction temperature, or by increasing the contact time (by decreasing the LHSV (space velocity)), the decrease of the yield of a lower olefin is suppressed, and the yield of a lower olefin can be stabilized over a long period of time.

In this case, although there is a possibility that the generation amount of aromatic hydrocarbon increases by the increase of reaction temperature or the decrease of space velocity, the generation amount of aromatic hydrocarbon also decreases with the lapse of time, and the decreasing trend of the generation amount of aromatic hydrocarbon with the lapse of time is not largely changed by the increase of the reaction temperature or the decrease of the space velocity, therefore, the possibility of increasing the aromatic hydrocarbon is low. In addition, the increase of reaction temperature with the lapse of time, and the decrease of space velocity of a feedstock (increase of contact time) may be performed alone, or the increase of reaction temperature and the decrease of space velocity may be performed in combination. Further, in a case where the increase of reaction temperature and the decrease of space velocity is performed in combination, the increase of reaction temperature and the decrease of space velocity may be performed at the same time, or may be performed respectively at different times. For example, in the continuous production, in the initial stage, the decrease of space velocity is performed, and in the late stage, the increase of reaction temperature is performed, or the decrease of space velocity and the increase of reaction temperature may also be performed in reverse. In addition, the increase of reaction temperature and the decrease of space velocity may be performed alternately, or the increase of reaction temperature and the decrease of space velocity may be performed at different frequencies, for example, the increase of reaction temperature is performed three times and then the decrease of space velocity is performed once, or the like.

Next, the method for regenerating a composite catalyst of the present embodiment will be described. In the present embodiment, for example, as compared with the case of using alumina as a binder, the catalyst lifetime can be extended by at least three times to five times or more, and further, as described above, by adjusting the reaction temperature or the space velocity (contact time), the catalyst lifetime can be extended by ten times or more. However, for example, in a case where the yield of a lower olefin is decreased down to the set value, it is required that the composite catalyst is replaced. In this case, in a case where the deterioration of a composite catalyst is caused by the generation of mainly coke, the composite catalyst can be regenerated by burning and removing the coke being carbon. In the burning and removing of coke, by burning the coke being carbon, which is deposited by supplying, for example, air diluted with nitrogen as inert gas in place of the feedstock gas, the coke can be removed as carbon dioxide.

In this case, the temperature is required to be a temperature at which coke is burned when coming into contact with oxygen, for example, the temperature of a reaction vessel is preferably 450° C. to 600° C., and more preferably 500° C.

to 550° C. This temperature range overlaps with the above-described reaction temperature range, but is a temperature range slightly lower than the reaction temperature range, and even if the heat generation is caused by burning, the burning is suppressed by diluting air with nitrogen as described above, and the temperature range is at the level of a temperature range in which a problem is not caused in a reaction vessel or in a composite catalyst. The deterioration of a composite catalyst is caused mainly by the deposition of carbon, therefore, by burning and removing the carbon, the composite catalyst can be regenerated in a state close to the initial state before using.

In the composite catalyst of the present embodiment, the method for producing the composite catalyst, and the method for producing a lower olefin, by using silica as a binder that is used for molding a powdery zeolite, the coke generation can be suppressed. Therefore, in the production of a lower olefin using a composite catalyst, a lower olefin can be continuously produced in a mild temperature range of around 530 to 650° C. (low temperature range in the production of a lower olefin), efficiently, and over a long period of time of 1000 hours or more. In addition, according to the method for regenerating a composite catalyst of the present embodiment, as described above, by regenerating the composite catalyst used over a long period of time, the composite catalyst can be further used for a long period of time.

EXAMPLES

Next, examples of the present invention will be described.

Example 1

At first, a synthesis method of a Na-type MFI zeolite (FeGaAl-MFI zeolite (Si/(Fe+Ga+Al)=121.3)) containing Ga and Al in Example 1 will be described.

A solution including 58.9 g of colloidal silica (30.6 wt % of $SiO_2$, 0.4 wt % of $Na_2O$, and 69.0 wt % of $H_2O$), and 1.69 g of sodium hydroxide was set to solution A, and a solution including 0.19 g of aluminum sulfate n-hydrate, 0.11 g of gallium nitrate n-hydrate, 0.24 g of iron nitrate 9-hydrate, 3.10 g of tetrapropylammonium bromide, and 187.8 g of purified water was set to solution B. The solution A and the solution B were gradually mixed at room temperature while stirring, and then the resultant mixture was vigorously stirred for 15 minutes in a mixer.

The mixed solution was left to stand overnight while keeping at a temperature of 60° C., and then a hydrothermal synthesis reaction was performed in an autoclave under the conditions of self-pressure, 150° C., 72 hours, and 300 rpm. After cooling, the resultant product was thoroughly washed with purified water. After that, drying was performed at 120° C. for 3 hours, and then firing was performed at 550° C. for 3 hours in the air flow to synthesize a FeGaAl-MFI zeolite. The elemental molar composition ratios of the zeolite were determined as Si/(Fe+Ga+Al)=121.3 (acid density), Fe/(Fe+Ga+Al)=0.4, Ga/(Fe+Ga+Al)=0.3, and Al/(Fe+Ga+Al)=0.3 by X-ray fluorescence measurement (see FIG. 1).

Next, a preparation method of a FeGaAl-MFI zeolite/silica composite catalyst (the mixture ratio of Zeolite/$SiO_2$ is 74 wt %/26 wt %) will be described.

A powdery Na-type FeGaAl-MFI zeolite synthesized in accordance with the above-described procedure, silica powder (product name: AEROSIL 200 manufactured by Evonik Degussa GmbH (limited company)) as a binder, and starch as a molding aid were mixed each in a predetermined amount, and then the resultant mixture was kneaded while adding an adequate amount of aqueous sodium hydroxide solution (having a NaOH concentration of 4.5 wt %) into the mixture to obtain a zeolite/silica mixture in a massive state. After that, the obtained massive mixture was processed into a cylindrical shape (1.0 mm φ) by an extruder, and the resultant product was dried at 120° C. for 3 hours and the fired at 550° C. for 3 hours under air circulation, and a FeGaAl-MFI zeolite/silica composite was obtained.

The composite was subjected to ion exchange by a 2.2 mol/L aqueous ammonium nitrate solution under boiling ref lux and then washed with water, this process was repeated four times (the ion exchange was performed for two hours per time, and the 2.2 mol/L aqueous ammonium nitrate solution was replaced with a new one each time), and then the resultant composite was dried at 120° C. for 3 hours and fired at 550° C. for 3 hours under air circulation, and a proton-type FeGaAl-MFI zeolite/silica composite catalyst was obtained. The weight composition ratio of the composite catalyst was determined as zeolite/silica=74 wt %/26 wt % by X-ray fluorescence measurement (see FIG. 1).

Next, a performance evaluation test method of a FeGaAl-MFI zeolite/silica composite catalyst (the mixture ratio of Zeolite/$SiO_2$ is 74 wt %/26 wt %) will be described.

The FeGaAl-MFI zeolite/silica composite in a cylindrical shape, which had been prepared in accordance with the above-described procedure, was sized so that the length is in a range of 1.0 to 2.0 mm and used as a catalyst sample for performance evaluation. In the reaction test, a catalytic cracking reaction of n-hexane was performed by a fixed bed flow reactor. A catalyst in a volume of 2.0 mL (1.32 gas the filling weight) was filled in a stainless steel reaction tube (made of SUS316) having an inner diameter of 12.6 mm so that the layer height of a catalyst layer is around 20 mm, and then glass wool was packed before and after the catalyst layer, and further alumina beads was filled before and after the glass wool.

As to the reaction conditions, under the conditions at a reaction temperature of 565° C., at a total pressure of 0.1 MPa, and a LHSV (liquid hourly space velocity) of n-hexane of 4.5 $h^{-1}$ (supply flow rate of n-hexane of 9.0 mL/h), a catalytic cracking reaction of n-hexane was performed for around 340 hours. Gas-phase and liquid-phase products were collected in around 30 hours from the start of the reaction, and subjected to gas chromatography analysis, the feedstock conversion rate (wt %) and each yield (wt %) of the lower olefins (ethylene and propylene) and the aromatic hydrocarbon were determined, and used as indicators of catalyst performance in an initial reaction stage. In addition, at every fixed time, a product was collected and subjected to gas chromatography analysis, and the changes over time of the catalyst performance were determined. Further, by a LECO-Carbon analytical method (analytical method using a carbon quantitative analyzer manufactured by LECO JAPAN CORPORATION by a combustion and non-dispersive infrared absorption method), an amount of the carbon deposited on the catalyst after the reaction test was measured. The summarized catalyst performance of the present sample, and the changes over time of the catalyst performance were shown in FIG. 2 and FIG. 5, respectively.

Example 2

Next, a synthesis method of a FeAl-MFI zeolite (Si/(Fe+Al)=120.3) in Example 2 will be described.

A Na-type FeAl-MFI zeolite was synthesized in the similar manner as in Example 1 except that a solution including 58.9 g of colloidal silica (30.6 wt % of $SiO_2$, 0.4 wt % of $Na_2O$, and 69.0 wt % of $H_2O$), and 1.69 g of sodium hydroxide was set to solution A, and a solution including 0.29 g of aluminum sulfate n-hydrate, 0.24 g of iron nitrate 9-hydrate, 3.10 g of tetrapropylammonium bromide, and 187.8 g of purified water was set to solution B. The elemental molar composition ratios of the zeolite were determined as Si/(Fe+Al)=120.3, Fe/(Fe+Al)=0.5, and Al/(Fe+Al)=0.5 by X-ray fluorescence measurement (see FIG. 1).

Next, a preparation method of a FeAl-MFI zeolite/silica composite catalyst (the mixture ratio of Zeolite/$SiO_2$ is 75 wt %/25 wt %) will be described.

By using a powdery Na-type FeAl-MFI zeolite synthesized in accordance with the above-described procedure, silica powder, and starch, molding and ion exchange were performed in the similar manner as in the Example 1, and a proton-type FeAl-MFI zeolite/silica composite catalyst in a cylindrical shape was obtained. The weight composition ratio of the composite catalyst was determined as zeolite/silica=75 wt %/25 wt % by X-ray fluorescence measurement (see FIG. 1).

Next, a performance evaluation test method of a FeAl-MFI zeolite/silica composite catalyst (the mixture ratio of Zeolite/$SiO_2$ is 75 wt %/25 wt %) will be described.

The FeAl-MFI zeolite/silica composite in a cylindrical shape, which had been prepared in accordance with the above-described procedure, was sized to be 1.0 to 2.0 mm and used as a catalyst sample for performance evaluation. The performance evaluation test was performed in the similar manner as in Example 1 except that the reaction time was changed to around 330 hours. Further, by a LECO-Carbon analytical method, an amount of the carbon deposited on the catalyst after the reaction test was measured. The summarized catalyst performance of the present sample was shown in FIG. 2.

Comparative Example 1

Next, a synthesis method of a FeGaAl-MFI zeolite (Si/(Fe+Ga+Al)=121.3) in Comparative Example 1 will be described.

A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement (see FIG. 1).

Next, a preparation method of a FeGaAl-MFI zeolite/alumina composite catalyst (the mixture ratio of Zeolite/$Al_2O_3$ is 77 wt %/23 wt %) will be described.

While adding an adequate amount of purified water into a powdery Na-type FeGaAl-MFI zeolite synthesized in accordance with the above-described procedure and alumina powder (CATALOID AP-1 manufactured by JGC Catalysts and Chemicals Ltd., $Al_2O_3$ content of 71.7 wt %), the powdery Na-type FeGaAl-MFI zeolite and the alumina powder were kneaded to obtain a zeolite/alumina mixture in a massive state. After that, the obtained massive mixture was processed into a cylindrical shape (1.0 mm $\phi$) by an extruder, and the resultant product was dried at 120° C. for 3 hours, and fired at 550° C. for 3 hours under air circulation, and a FeGaAl-MFI zeolite/alumina composite was obtained. The composite was subjected to ion exchange by a 2.2 mol/L aqueous ammonium nitrate solution under boiling reflux and then washed with water, this process was repeated four times (the ion exchange was performed for two hours per time, and the 2.2 mol/L aqueous ammonium nitrate solution was replaced with a new one each time), and then the resultant product was dried at 120° C. for 3 hours, and fired at 550° C. for 3 hours under air circulation, and a proton-type FeGaAl-MFI zeolite/alumina composite catalyst was obtained. The weight composition ratio of the composite catalyst was determined as zeolite/alumina=77 wt %/23 wt % by X-ray fluorescence measurement (see FIG. 1).

Next, a performance evaluation test method of a FeGaAl-MFI zeolite/alumina composite catalyst (the mixture ratio of Zeolite/$Al_2O_3$ is 77 wt %/23 wt %) will be described.

The FeGaAl-MFI zeolite/alumina composite in a cylindrical shape, which had been prepared in accordance with the above-described procedure, was sized to be 1.0 to 2.0 mm and used as a catalyst sample for performance evaluation. The reaction test was performed in the similar manner as in Example 1 except that the LHSV of n-hexane was changed to 5.0 $h^{-1}$ (the supply flow rate of n-hexane of 10.0 mL/h), and the reaction time was changed to around 100 hours. Further, by a LECO-Carbon analytical method, an amount of the carbon deposited on the catalyst after the reaction test was measured. The summarized catalyst performance of the present sample, and the changes over time of the catalyst performance were shown in FIG. 2 and FIG. 5, respectively.

In the sample molded and composited with a FeGaAl-MFI zeolite and an alumina binder (Comparative Example 1), although the initial propylene yield showed a high value of around 18 wt %, as can be seen from the changes over time in FIG. 5, the decrease of the yield was observed from around the time after the lapse of 80 hours, and the apparent decrease of the catalyst performance was confirmed after the lapse of 100 hours. On the other hand, in a sample molded and composited at the approximately same mixture ratio as that of the sample in Comparative Example 1 by using silica as a binder (Example 1), although the initial propylene yield was slightly low, the yield of aromatic was suppressed low, and as a result, a catalyst lifetime of 340 hours or longer was achieved (see FIG. 5).

When the amount of the carbon deposited on a catalyst after the reaction test was measured, the deposition amount was 24 wt % in 100 hours in the sample using an alumina binder and was 4.8 wt % in 340 hours in the sample using a silica binder (FIG. 2), accordingly it was found that the deposited carbon amount is reduced down to ⅕ or less. In addition, also as to the FeGaAl-MFI zeolite, by using a sample molded and composited with a silica binder (Example 2), the similar effect was observed (FIG. 2). By molding and compounding with a silica binder, the acid point on an outer surface of a zeolite was covered and inactivated, and the generation of aromatic was suppressed, accordingly the suppressing ability of carbon deposition was significantly improved, and as a result, it was confirmed that longer catalyst lifetime is given.

Example 3

Next, a synthesis method of a FeGaAl-MFI zeolite (Si/(Fe+Ga+Al)=121.3) in Example 3 will be described. A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement (see FIG. 3).

Next, a preparation method of a FeGaAl-MFI zeolite/silica composite catalyst (the mixture ratio of Zeolite/SiO$_2$ is 68 wt %/32 wt %) will be described.

By using a powdery Na-type FeGaAl-MFI zeolite synthesized in accordance with the above-described procedure, silica powder, and starch, molding and ion exchange were performed in the similar manner as in the Example 1, and proton-type FeGaAl-MFI zeolite/silica composite catalysts in a cylindrical shape, in which each mixture ratio was changed, were prepared. The weight composition ratio of the composite catalyst was determined as zeolite/silica=68 wt %/32 wt % by X-ray fluorescence measurement (see FIG. 3).

Next, a performance evaluation test method of a FeGaAl-MFI zeolite/silica composite catalyst (the mixture ratio of Zeolite/SiO$_2$ is 68 wt %/32 wt %) will be described.

The FeGaAl-MFI zeolite/silica composite in a cylindrical shape, which had been prepared in accordance with the above-described procedure, was sized so that the length is in a range of 1.0 to 2.0 mm and used as a catalyst sample for performance evaluation. In the reaction test, a catalytic cracking reaction of n-hexane was performed by a fixed bed flow reactor. A catalyst in an amount of 1.44 g (zeolite content of 0.98 g, 2.0 mL as the filling volume) was filled in a stainless steel reaction tube (made of SUS316) having an inner diameter of 12.6 mm, glass wool was packed before and after the catalyst layer, and further alumina beads was filled before and after the glass wool.

As to the reaction conditions, under the conditions at a reaction temperature of 565° C., at a total pressure of 0.1 MPa, and a WHSV (weight hourly space velocity) of n-hexane of 6.0 h$^{-1}$ (supply flow rate of n-hexane of 5.9 g/h), a catalytic cracking reaction of n-hexane was performed for around 360 hours. Gas-phase and liquid-phase products were collected in around 30 hours from the start of the reaction, and subjected to gas chromatography analysis, the feedstock conversion rate (wt %) and each yield (wt %) of the lower olefins (ethylene and propylene) and the aromatic hydrocarbon were determined, and used as indicators of catalyst performance in an initial reaction stage. In addition, at every fixed time, a product was collected and subjected to gas chromatography analysis, and the changes over time of the catalyst performance were determined. Further, by a LECO-Carbon analytical method, an amount of the carbon deposited on the catalyst after the reaction test was measured. The summarized catalyst performance of the present sample was shown in FIG. 4.

Example 4

Next, a synthesis method of a FeGaAl-MFI zeolite (Si/(Fe+Ga+Al)=121.3) in Example 4 will be described. A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement (see FIG. 3).

Next, a preparation method of a FeGaAl-MFI zeolite/silica composite catalyst (the mixture ratio of Zeolite/SiO$_2$ is 90 wt %/10 wt %) will be described.

By using a powdery Na-type FeGaAl-MFI zeolite synthesized in accordance with the above-described procedure, silica powder, and starch, molding and ion exchange were performed in the similar manner as in the Example 1, and proton-type FeGaAl-MFI zeolite/silica composite catalysts in a cylindrical shape, in which each mixture ratio was changed, were prepared. The weight composition ratio of the composite catalyst was determined as zeolite/silica=90 wt %/10 wt % by X-ray fluorescence measurement (see FIG. 3).

Next, a performance evaluation test method of a FeGaAl-MFI zeolite/silica composite catalyst (the mixture ratio of Zeolite/SiO$_2$ is 90 wt %/10 wt %) will be described.

The FeGaAl-MFI zeolite/silica composite in a cylindrical shape, which had been prepared in accordance with the above-described procedure, was sized to be 1.0 to 2.0 mm and used as a catalyst sample for performance evaluation. The reaction test was performed in the similar manner as in Example 3 except that the catalyst filling amount was changed to 1.09 g (the zeolite content of 0.98 g, and 2.0 mL as the filling volume), and the reaction time was changed to around 480 hours. Further, by a LECO-Carbon analytical method, an amount of the carbon deposited on the catalyst after the reaction test was measured.

The summarized catalyst performance of the present sample, and the changes over time of the catalyst performance were shown in FIG. 4 and FIG. 5, respectively.

FIG. 4 shows the summarized catalyst performance of each FeGaAl-MFI/SiO$_2$ composite catalyst having a different mix composition. Three kinds of samples having a different content of zeolite from each other (68 wt %, 74 wt %, and 90 wt %) were prepared, and when each initial performance was examined, as the content of zeolite became higher, the reaction conversion rate, the lower olefin yield, and the aromatic yield were increased. In addition, even if any of the samples was used, each aromatic yield was suppressed to a low value of 5.0 wt % or less, and as a result, a catalyst lifetime of 340 hours or longer was realized. Especially, even in a sample having a high zeolite content (90 wt %, in Example 4), the initial aromatic yield was suppressed as low as 4.6 wt %, as a result, an extremely long catalyst lifetime of 480 hours or longer was achieved (see FIG. 5).

Accordingly, it was confirmed that the composite catalyst by a silica binder gives a high propylene yield in a wide range of silica mixing ratio (around 10 to 30 wt %), and a long catalyst lifetime at the same time.

Example 5

Next, a synthesis method of a FeGaAl-MFI zeolite (Si/(Fe+Ga+Al)=121.3) in Example 5 will be described.

A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement.

Next, a preparation method of a FeGaAl-MFI zeolite/silica composite catalyst (the mixture ratio of Zeolite/SiO$_2$ is 90 wt %/10 wt %) will be described.

A proton-type FeGaAl-MFI zeolite/silica composite catalyst in a cylindrical shape was prepared in the similar manner as in Example 4. The weight composition ratio of the composite catalyst was determined as zeolite/silica=90 wt %/10 wt % by X-ray fluorescence measurement (see FIG. 6).

Next, a performance evaluation test method of a FeGaAl-MFI zeolite/silica composite catalyst (the mixture ratio of Zeolite/SiO$_2$ is 90 wt %/10 wt %) will be described.

The FeGaAl-MFI zeolite/silica composite in a cylindrical shape, which had been prepared in accordance with the above-described procedure, was sized to be 1.0 to 2.0 mm and used as a catalyst sample for performance evaluation. The reaction test was performed in the similar manner as in Example 4 except that the LHSV of n-hexane was changed to 6.0 h$^{-1}$ (the supply flow rate of n-hexane of 12.0 mL/h), and the reaction time was changed to around 30 hours (the sampling was performed in 5, 24, and 30 hours from the start of the reaction). The initial catalyst performance of the present sample was shown in FIG. 6.

Example 6

Next, a synthesis method of a FeGaAl-MFI zeolite (Si/(Fe+Ga+Al)=121.3) in Example 6 will be described.

A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement.

Next, a preparation method of a FeGaAl-MFI zeolite/silica composite catalyst (the mixture ratio of Zeolite/SiO$_2$ is 90 wt %/10 wt %) will be described.

A proton-type FeGaAl-MFI zeolite/silica composite catalyst in a cylindrical shape was prepared in the similar manner as in Example 4. The weight composition ratio of the composite catalyst was determined as zeolite/silica=90 wt %/10 wt % by X-ray fluorescence measurement (see FIG. 6).

Next, a performance evaluation test method of a FeGaAl-MFI zeolite/silica composite catalyst (the mixture ratio of Zeolite/SiO$_2$ is 90 wt %/10 wt %) will be described.

The FeGaAl-MFI zeolite/silica composite in a cylindrical shape, which had been prepared in accordance with the above-described procedure, was sized to be 1.0 to 2.0 mm and used as a catalyst sample for performance evaluation. The reaction test was performed in the similar manner as in Example 4 except that the LHSV of n-hexane was changed to 7.0 h$^{-1}$ (the supply flow rate of n-hexane of 14.0 mL/h), and the reaction time was changed to around 30 hours (the sampling was performed in 5, 24, and 30 hours from the start of the reaction). The initial catalyst performance of the present sample was shown in FIG. 6.

Comparative Example 2

Next, a synthesis method of a FeGaAl-MFI zeolite (Si/(Fe+Ga+Al)=121.3) in Comparative Example 2 will be described.

A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement.

Next, a preparation method of a FeGaAl-MFI zeolite/silica composite catalyst (the mixture ratio of Zeolite/SiO$_2$ is 90 wt %/10 wt %) will be described.

A proton-type FeGaAl-MFI zeolite/silica composite catalyst in a cylindrical shape was prepared in the similar manner as in Example 4. The weight composition ratio of the composite catalyst was determined as zeolite/silica=90 wt %/10 wt % by X-ray fluorescence measurement (see FIG. 6).

Next, a performance evaluation test method of a FeGaAl-MFI zeolite/silica composite catalyst (the mixture ratio of Zeolite/SiO$_2$ is 90 wt %/10 wt %) as Comparative Example 2 will be described.

The FeGaAl-MFI zeolite/silica composite in a cylindrical shape, which had been prepared in accordance with the above-described procedure, was sized to be 1.0 to 2.0 mm and used as a catalyst sample for performance evaluation. The reaction test was performed in the similar manner as in Example 4 except that the LHSV of n-hexane was changed to 15.0 h$^{-1}$ (the supply flow rate of n-hexane of 30.0 mL/h), and the reaction time was changed to around 30 hours (the sampling was performed in 5, 24, and 30 hours from the start of the reaction). The initial catalyst performance of the present sample was shown in FIG. 6.

FIG. 6 shows the effect of LHSV (contact time) summarized in the initial performance of a FeGaAl-MFI/SiO$_2$ composite catalyst. Based on Example 4, as the LHSV increased 4.5→6.0→7.0→15.0 h$^{-1}$ (shortening the contact time), the reaction conversion rate, the lower olefin yield, and the aromatic yield were each gradually lowered, but the decrease of the propylene yield at a LHSV of 4.5 to 7.0 h$^{-1}$ was extremely small (15.6→15.1 wt %). On the other hand, the aromatic yield was lowered to around half the yield (4.6→2.2 wt %). Therefore, it was confirmed that a composite catalyst using a silica binder gives a high propylene yield exceeding 15 wt % in a wide range of LHSV (contact time). In addition, in FIG. 6, by setting each contact time with n-hexane to 0.23 (Example 4), 017 (Example 5), 0.14 (Example 6), and 0.07 (Comparative Example 2), the contact time showing the reciprocal of the LHSV, as the reciprocal of the LHSV of 4.5, 6.0, 7.0, and 15.0 h$^{-1}$, each experiment was performed.

Example 7

Next, a synthesis method of a FeGaAl-MFI zeolite (Si/(Fe+Ga+Al)=121.3) in Example 7 will be described.

A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement.

Next, a preparation method of a FeGaAl-MFI zeolite/silica composite catalyst (the mixture ratio of Zeolite/SiO$_2$ is 90 wt %/10 wt %) will be described.

A proton-type FeGaAl-MFI zeolite/silica composite catalyst in a cylindrical shape was prepared in the similar manner as in Example 4. The weight composition ratio of the composite catalyst was determined as zeolite/silica=90 wt %/10 wt % by X-ray fluorescence measurement (see FIG. 7).

Next, a performance evaluation test method of a FeGaAl-MFI zeolite/silica composite catalyst (the mixture ratio of Zeolite/SiO$_2$ is 90 wt %/10 wt %) will be described.

The FeGaAl-MFI zeolite/silica composite in a cylindrical shape, which had been prepared in accordance with the above-described procedure, was sized to be 1.0 to 2.0 mm and used as a catalyst sample for performance evaluation. The reaction test was performed in the similar manner as in Example 5 except that the reaction temperature was changed to 585° C., and the reaction time was changed to around 15 hours (the sampling was performed in 5, and 15 hours from the start of the reaction). The initial catalyst performance of the present sample was shown in FIG. 7.

Example 8

Next, a synthesis method of a FeGaAl-MFI zeolite (Si/(Fe+Ga+Al)=121.3) in Example 8 will be described. A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement.

Next, a preparation method of a FeGaAl-MFI zeolite/silica composite catalyst (the mixture ratio of Zeolite/SiO$_2$ is 90 wt %/10 wt %) will be described.

A proton-type FeGaAl-MFI zeolite/silica composite catalyst in a cylindrical shape was prepared in the similar manner as in Example 4. The weight composition ratio of the composite catalyst was determined as zeolite/silica=90 wt %/10 wt % by X-ray fluorescence measurement (see FIG. 7).

Next, a performance evaluation test method of a FeGaAl-MFI zeolite/silica composite catalyst (the mixture ratio of Zeolite/SiO$_2$ is 90 wt %/10 wt %) will be described.

The FeGaAl-MFI zeolite/silica composite in a cylindrical shape, which had been prepared in accordance with the above-described procedure, was sized to be 1.0 to 2.0 mm and used as a catalyst sample for performance evaluation. The reaction test was performed in the similar manner as in Example 5 except that the reaction temperature was changed to 635° C., and the reaction time was changed to around 15 hours (the sampling was performed in 5, and 15 hours from the start of the reaction). The initial catalyst performance of the present sample was shown in FIG. 7.

FIG. 7 shows the effect of reaction temperature summarized in the initial performance of a FeGaAl-MFI/SiO$_2$ composite catalyst. Based on Example 5, as the temperature increased 565° C.→585→635° C., the reaction conversion rate, the lower olefin yield, and the aromatic yield were improved, and at 635° C., lower olefin yields as high as 13.3 wt % of ethylene yield and 20.5 wt % of propylene yield were achieved. On the other hand, the aromatic yield was 6.5 wt % even at 635° C., and lower than the value (7.3 wt %, see FIG. 2) in the reaction test at 565° C. using a composite catalyst with an alumina binder (Comparative Example 1). Therefore, it was confirmed that a composite catalyst using a silica binder gives a high yield of a lower olefin while suppressing the aromatic generation, even when being used for catalytic cracking at a high reaction temperature exceeding 600° C.

Example 9

Next, a synthesis method of a FeGaAl-MFI zeolite (Si/(Fe+Ga+Al)=121.3) in Example 9 will be described.

A Na-type FeGaAl-MFI zeolite was synthesized in the similar manner as in Example 1. The elemental molar composition ratios of the zeolite were determined as Si/(Fe+Ga+Al)=121.3, Fe/(Fe+Ga+Al)=0.4, Ga/(Fe+Ga+Al)=0.3, and Al/(Fe+Ga+Al)=0.3 by X-ray fluorescence measurement.

Next, a preparation method of a FeGaAl-MFI zeolite/silica composite catalyst (the mixture ratio of Zeolite/SiO$_2$ is 90 wt %/10 wt %) will be described.

A proton-type FeGaAl-MFI zeolite/silica composite catalyst in a cylindrical shape was prepared in the similar manner as in Example 4. The weight composition ratio of the composite catalyst was determined as zeolite/silica=90 wt %/10 wt % by X-ray fluorescence measurement.

Next, a performance evaluation test method of a FeGaAl-MFI zeolite/silica composite catalyst (the mixture ratio of Zeolite/SiO$_2$ is 90 wt %/10 wt %) will be described.

The FeGaAl-MFI zeolite/silica composite in a cylindrical shape, which had been prepared in accordance with the above-described procedure, was sized to be 1.0 to 2.0 mm and used as a catalyst sample for performance evaluation. By using the same reaction test apparatus as those in Examples 1 to 8, and by setting the catalyst filling amount to 2.0 mL and the total pressure to 0.1 MPa (the filling method of a catalyst was also similar to those in Examples 1 to 8), around 1,000 hours of a n-hexane catalytic cracking reaction was performed under the following operating conditions.

Step 1 (from the start of the reaction to the lapse of around 200 hours): the reaction temperature was set to 565° C., and the LHSV of n-hexane was set to 7.0 h$^{-1}$.

Step 2 (from around 200 hours to around 380 hours after the start of the reaction): the reaction temperature was kept at 565° C., and the LHSV of n-hexane was set to 6.0 h$^{-1}$ to extend the contact time with n-hexane.

Step 3 (from around 380 hours to around 540 hours after the start of the reaction): the reaction temperature was kept at 565° C., and the LHSV of n-hexane was set to 5.0 h$^{-1}$ to extend the contact time with n-hexane.

Step 4 (from around 540 hours to around 620 hours after the start of the reaction): the reaction temperature was kept at 565° C., and the LHSV of n-hexane was set to 4.5 h$^{-1}$ to extend the contact time with n-hexane.

Step 5 (from around 620 hours to around 740 hours after the start of the reaction): the reaction temperature was increased to 570° C., and the LHSV of n-hexane was retained at 4.5 h$^{-1}$.

Step 6 (from around 740 hours to around 835 hours after the start of the reaction): the reaction temperature was increased to 580° C., and the LHSV of n-hexane was retained at 4.5 h$^{-1}$.

Step 7 (from around 835 hours to around 920 hours after the start of the reaction): the reaction temperature was increased to 585° C., and the LHSV of n-hexane was retained at 4.5 h$^{-1}$.

Step 8 (from around 920 hours to around 1,000 hours after the start of the reaction): the reaction temperature was increased to 595° C., and the LHSV of n-hexane was retained at 4.5 h$^{-1}$.

After the reaction was started under the above-described operating conditions, at every fixed time, a product was collected and subjected to gas chromatography analysis, and the changes over time of the catalyst performance were determined. The changes over time of the catalyst performance of the present sample were shown in FIG. 8 (changes over time of the conversion rate of n-hexane and the ethylene yield/the propylene yield) and FIG. 9 (changes over time of the conversion rate of n-hexane and the aromatic hydrocarbon yield).

From the examination results in Examples 4 to 8, the findings that the decrease of the propylene yield in a range of LHSV of 4.5 to 7.0 h$^{-1}$ (the reaction temperature was fixed at 565° C.) is extremely small, and that the aromatic yield at a reaction temperature of up to around 635° C. is suppressed low (the LHSV was fixed at 6.0 h$^{-1}$) were obtained. Accordingly, it was examined how long the catalyst lifetime can be extended by appropriately combining the operation factors that significantly affect on the aromatic generation (catalyst lifetime). As the catalyst sample, a FeGaAl-MFI/SiO$_2$ composite catalyst that had been used in Examples 4 to 8 was used, as the conditions at the time of starting the reaction, the reaction temperature was set to 565° C. and the LHSV was set to 7.0 h$^{-1}$ so that the aromatic yield is suppressed lower, and the reaction was started. The compensation operation was performed by lowering the LHSV sequentially to 7.0→6.0→4.5h$^{-1}$ (extending the contact time) along with the decrease in catalyst performance (reaction conversion rate), the reaction conversion rate was increased and the propylene yield was maintained. After that, the LHSV was fixed to 4.5 h$^{-1}$, and the compensation operation was performed by sequentially increasing the reaction temperature to 565° C.→570° C.→580° C.→585°

C.→595° C., and similarly, the reaction conversion rate was increased and the propylene yield was maintained. It was confirmed that by controlling these operation conditions, the catalyst lifetime can be sustained for 1,000 hours or more (see FIGS. 8 and 9).

Example 10

Next, a synthesis method of a FeGaAl-MFI zeolite (Si/(Fe+Ga+Al)=31.3) in Example 10 will be described.

A Na-type FeGaAl-MFI zeolite was synthesized in the similar manner as in Example 1 except that a solution including 58.9 g of colloidal silica (30.6 wt % of $SiO_2$, 0.4 wt % of $Na_2O$, and 69.0 wt % of $H_2$), and 2.25 g of sodium hydroxide was set to solution A, and a solution including 0.76 g of aluminum sulfate n-hydrate, 0.44 g of gallium nitrate n-hydrate, 0.98 g of iron nitrate 9-hydrate, 4.65 g of tetrapropylammonium bromide, and 187.2 g of purified water was set to solution B. The elemental molar composition ratios of the zeolite were determined as Si/(Fe+Ga+Al)=31.3, Fe/(Fe+Ga+Al)=0.4, Ga/(Fe+Ga+Al)=0.3, and Al/(Fe+Ga+Al)=0.3 by X-ray fluorescence measurement.

Next, a preparation method of a FeGaAl-MFI zeolite/silica composite catalyst (the mixture ratio of Zeolite/$SiO_2$ is 65 wt %/35 wt %) will be described.

By using a powdery Na-type FeGaAl-MFI zeolite synthesized in accordance with the above-described procedure, silica powder, and starch, a proton-type FeGaAl-MFI zeolite/silica composite catalyst in a cylindrical shape was prepared by performing the molding and ion exchange in the similar manner as in Example 3. The weight composition ratio of the composite catalyst was determined as zeolite/silica=65 wt %/35 wt % by X-ray fluorescence measurement.

Next, a catalyst regeneration test method of a FeGaAl-MFI zeolite/silica composite catalyst (the mixture ratio of Zeolite/$SiO_2$ is 65 wt %/35 wt %) will be described.

The FeGaAl-MFI zeolite/silica composite in a cylindrical shape, which had been prepared in accordance with the above-described procedure, was sized to be 1.0 to 2.0 mm and used as a catalyst sample for performance evaluation. The reaction test was performed in the similar manner as in Example 1 except that the reaction time was changed to around 45 hours (the sampling was performed in 2, 20, 28, 32, and 44 hours from the start of the reaction). In addition, the reaction test was stopped once at the point of time when the around 45 hours elapsed from the start of the reaction, and a regeneration process of the catalyst (burning and removing of the carbon deposited on the catalyst) was performed under the following operating conditions.

Step 1: the supplying of a n-hexane feedstock to a reactor was stopped, and the temperature was naturally cooled down to room temperature under nitrogen flow.

Step 2: the catalyst layer temperature was gradually raised up to around 100° C., and then retained for one hour while supplying the air diluted with nitrogen (having an oxygen concentration of 0.5 vol %) at a flow rate of around 67 NL/h.

Step 3: the catalyst layer temperature was gradually raised up to around 350° C., and then retained for one hour while supplying the air diluted with nitrogen (having an oxygen concentration of 0.5 vol %) at a flow rate of around 67 NL/h.

Step 4: the catalyst layer temperature was gradually raised up to around 450° C., and then retained for two hours while supplying the air diluted with nitrogen (having an oxygen concentration of 0.5 vol %) at a flow rate of around 67 NL/h.

Step 5: the catalyst layer temperature was gradually raised up to around 500° C., and then retained for 18 hours while supplying the air diluted with nitrogen (having an oxygen concentration of 1.0 vol %) at a flow rate of around 67 NL/h.

Step 6: the catalyst layer temperature was retained at around 500° C. for one hour while supplying the air diluted with nitrogen (having an oxygen concentration of 2.0 vol %) at a flow rate of around 67 NL/h.

Step 7: the catalyst layer temperature was gradually raised up to around 535° C., and then retained for two hours while supplying the air diluted with nitrogen (having an oxygen concentration of 2.0 vol %) at a flow rate of around 67 NL/h.

Step 8: the flowing gas was switched to pure nitrogen, and then the heating of the catalyst layer was stopped and naturally cooled down to the room temperature.

After the above-described catalyst regeneration process was performed, the reaction test was resumed under the same conditions as those of the initial reaction test except for the sampling period of the product (the sampling was performed in 2, 5, 20, 27, and 44 hours from the start of the reaction). FIG. 10 shows the changes over time of the catalyst performance (conversion rate of n-hexane).

The regeneration of a catalyst was examined in the present Example. In the present Example, only the hydrocarbon feedstock was supplied to a catalyst without using a diluent such as steam in the reaction feedstock, therefore, it may be considered that the deterioration factor of the catalytic activity is basically only the deposition of carbon. Accordingly, the catalytic activity recovers and can be repeatedly used by removing the deposited carbon. Therefore, the catalyst reaction test was performed (the catalytic activity was lowered in a short time by using a sample having a large acid density (Si/(Fe+Ga+Al)=31.3) in the present Example), the reaction was once stopped when the decrease of the activity was observed, and the air (having an oxygen concentration of 0.5 to 2.0 vol %) diluted in accordance with the above-described operation method (Steps 1 to 8) was supplied and the carbon was burned and removed.

When the reaction test was resumed after the regeneration process, it was observed that the reaction conversion rate changed following the similar history to that in the first reaction test (see FIG. 10), and accordingly it was confirmed that the burning and removing processing of the carbon had been appropriately performed. Therefore, according to the present invention, it was confirmed that by using a FeGaAl-MFI zeolite or a FeAl-MFI zeolite, which is molded and composited with a silica binder, under the appropriate conditions, the efficient propylene production is sustained for an extremely long time, and further the catalyst with lowered activity is regenerated by a burning and removing processing of the carbon, and can be repeatedly used.

The invention claimed is:

1. A composite catalyst for producing a lower olefin from a hydrocarbon feedstock, comprising:
    a zeolite being a crystalline aluminosilicate containing gallium and iron or iron in the framework of the zeolite and further having a framework with 8- to 12-membered ring; and
    silicon dioxide,
    wherein
    when the zeolite is a crystalline aluminosilicate containing iron and gallium, and
    an acid density as a composition ratio of the number of moles of silicon to a sum of the number of moles of iron, gallium, and aluminum is 75.0 to 200.0, a composition ratio of the number of moles of gallium to a sum of the number of moles of iron, gallium, and aluminum is 0.1 to 0.4, and a composition ratio of the number of moles of iron to a sum of the number of moles of iron, gallium, and aluminum is 0.2 to 0.6, and when the zeolite is a crystalline aluminosilicate containing iron, and an acid density as a composition ratio of the number of moles of silicon to a sum of the number of moles of iron and aluminum is 75.0 to 200.0, and a composition ratio of the number of moles of iron to a sum of the number of moles of iron and aluminum is 0.4 to 0.7.

2. The composite catalyst according to claim 1, wherein the zeolite is a crystalline aluminosilicate containing iron and gallium, and an acid density as a composition ratio of the number of moles of silicon to a sum of the number of moles of iron, gallium, and aluminum is 75.0 to 200.0, a composition ratio of the number of moles of gallium to a sum of the number of moles of iron, gallium, and aluminum is 0.1 to 0.4, and a composition ratio of the number of moles of iron to a sum of the number of moles of iron, gallium, and aluminum is 0.2 to 0.6.

3. The composite catalyst according to claim 1, wherein the zeolite is a crystalline aluminosilicate containing iron, and an acid density as a composition ratio of the number of moles of silicon to a sum of the number of moles of iron and aluminum is 75.0 to 200.0, and a composition ratio of the number of moles of iron to a sum of the number of moles of iron and aluminum is 0.4 to 0.7.

4. The composite catalyst according to claim 1, wherein a concentration of the silicon dioxide is 5 to 50 wt %.

5. A method for producing the composite catalyst according to claim 1, comprising:

a hydrothermal synthesis process, a molding process, and an ion exchange process.

6. The method for producing the composite catalyst according to claim 5, wherein in the molding process, an alkaline aqueous solution containing starch is used in molding a mixture of a zeolite and silicon dioxide.

7. A method for producing a lower olefin, producing comprising contacting a hydrocarbon feedstock with the composite catalyst according to claim 1, wherein a gas containing 15 wt % or more of the hydrocarbon feedstock is supplied to the composite catalyst, and the producing of the lower olefin from the hydrocarbon feedstock proceeds in a temperature range of 530° C. to 650° C.

8. A method for producing a lower olefin, producing comprising contacting a hydrocarbon feedstock with the composite catalyst according to claim 1, wherein a gas containing 15 wt % or more of the hydrocarbon feedstock is supplied to the composite catalyst, and a contact time of the hydrocarbon feedstock with the composite catalyst is 0.08 to 1.0 h.

9. The method for producing a lower olefin according to claim 7, further comprising a regenerating step, wherein air diluted with inert gas is supplied to the composite catalyst, and deposited carbon is burned and removed in a temperature range of 450° C. to 600° C.

10. The composite catalyst according to claim 1, wherein the zeolite is an MFI zeolite.

11. The composite catalyst according to claim 1, wherein a concentration of the silicon dioxide is 5 to 40 wt %.

* * * * *